United States Patent [19]

Denninger et al.

[11] 4,093,440

[45] June 6, 1978

[54] SOLID PHYTOSANITARY COMPOSITION

[75] Inventors: Claude Denninger, Chazay d'Azergues; Michel Joly, Villeurbanne; Jean-Noel Tabet, Lyon, all of France

[73] Assignee: Sogemaric, Lyon, France

[21] Appl. No.: 594,856

[22] Filed: Jul. 10, 1975

[30] Foreign Application Priority Data

Jul. 15, 1974 France .................................. 74 25780

[51] Int. Cl.² ............................................. A01N 17/08
[52] U.S. Cl. ........................................ 71/65; 71/64 A;
    71/64 F; 71/79; 71/116; 71/117; 71/DIG. 1;
    239/310; 424/141; 424/203; 424/213; 424/273
    R; 424/286; 424/345; 424/352; 424/361
[58] Field of Search ............ 424/361; 71/64 A, 64 F,
    71/65, 79, 116, 117; 239/310, 315, 317

[56] References Cited

U.S. PATENT DOCUMENTS

| 3,083,916 | 4/1963 | Neel | 239/310 |
|---|---|---|---|
| 3,338,700 | 8/1967 | Barron | 71/64 A |
| 3,920,442 | 11/1975 | Albert et al. | 424/361 |

OTHER PUBLICATIONS

Chemical Abstracts, vol. 72 (1970), p. 30744z.

*Primary Examiner*—V. D. Turner
*Attorney, Agent, or Firm*—McDougall, Hersh & Scott

[57] ABSTRACT

Solid phytosanitary compositions compacted into single doses for agricultural application and intended to be progressively disintegrated by contact with a stream of water and containing at least one active pesticide, at least non non-hydrophilid filler, and at least one wetting agent, dispersant or deflocculant, and a large quantity of a solid, water-insoluble disintegrating agent, such as starch.

6 Claims, No Drawings

SOLID PHYTOSANITARY COMPOSITION

This invention relates to solid pesticide compositions for agricultural application which are intended to be progressively disintegrated by contact with a stream of water.

More particularly, the invention relates to solid pesticide compositions for use in the treatment of amateur gardens by a new method which, so far as the user is concerned, eliminates the need for any complicated and/or dangerous handling of pesticides.

The treatment of trees, vegetables or flowers growing in amateur gardens involves specific problems due to a certain level of ignorance among amateur gardeners of the potential dangers presented by phytosanitary products.

The plants treated, in respect of which it is essential to keep to the stipulated doses on account of the phytotoxicity phenomena to which excessive doses can give rise, are the primary concern because, very often, the amateur gardener has a tendency to increase the dose in the hope of obtaining a better effect whereas, in fact, increased doses can cause irreparable damage to the plants.

Another disadvantage of overdosage is the release into the atmosphere of excessive quantitites of pesticides which are incompatible with protection of the environment and with legislation on the use of pesticides.

Another danger, this time involving the user, is the need for difficult manipulation of small quantities of more or less toxic products which very often are in the form of extremely fine powders which are readily blown away by wind and, for this reason, are difficult and, in some cases, dangerous to handle.

Accordingly, it is extremely important for these three reasons to develop and make available to amateur gardeners formulations and devices which eliminate the disadvantages referred to above.

The present invention responds to this need by providing a formulation in the form of single compact doses.

This type of formulation eliminates the dangers of overdosage but, to give satisfaction, it must be uniformly disintegrable in dependence upon the volume of water with which it is brought into contact. In other words, the quantity of disintegrated material must be substantially proportional to the volume of water.

This effect is obtained in known manner in the pharmaceutical industry in the form of tablets which are obtained by the compression of a powder with various additives, especially binders. However, they cannot be used for the application of pesticides to plants on account of the very small quantities of disintegrated material per liter of disintegrating liquid, because the active material has to be applied to the plants in quantities sufficient to obtain the required effect.

The invention provides a solution to this problem. The invention relates to solid, compact, pesticide compositions for agricultural application which are intended to be progressively disintegrated by contact with a stream of water and which are distinquished by the fact that they contain, in addition to the active phytosanitary materials and, optionally, wetting agents and/or dispersants of the type normally used in the production of wettable powders, a solid water-insoluble disintegrating agent. If the wettable powder is intended to contain a solid filler, the filler used should not have hydrophilic properties.

In the context of the invention, a solid non-hydrophilic filler is a powder-form solid without any tendency to hydrate in aqueous medium, because a composition containing a hydrophilic filler in contact with water gives a tacky paste which slows down disintegration to a considerable extent.

In the context of the invention, a "phytosanitary active material" is essentially a herbicide, insecticide, fungicide, growth regulator, bactericide or fertilizer which may be applied to plants or seeds. According to the invention, the compositions may contain one or more active materials which, together, may represent a few per cent to 80% by weight of the composition.

In the context of the invention, the solid disintegrating agent should be insoluble in water which does not mean that it should not be hydratable or swellable in water. This is the case with starches based on such vegetables as corn, rice, potatoes, which give good results, although maize starch is preferred. However, this list is by no means complete and it is possible to use compounds with an equivalent function due, for example, to a polyholoside structure similar to that of starch.

The disintegrating agent must be present in a sufficient quantity to insure that the rate of disintegration, i.e. the quantity of solid active material disintegrated per liter of water, is high enough to enable the plants to be effectively treated.

By contrast, an excess of this additive causes excessively rapid disintegration. Generally, quantities of from 20% to 60% by weight of the composition are perfectly suitable. However, this is by no means limitative and quantities outside these limits may be used provided that an adequate rate of disintegration, for example approximately 2 to 15 g/l, is obtained.

In order to prepare the compositions according to the invention, a mixture of one or more active phytosanitary materials (herbicides, growth regulators, insecticides, fungicides) in solid form, i.e. either the active material alone if it is solid, or impregnated on a solid, inert support if it is liquid, is mixed with the additives, wetting agents, dispersants of the type commonly used in the production of wettable powders, and with the non-hydrophilic filler and the disintegrating agent described above. The mixture is homogenized and then compressed into tablets or pellets of the required shape under a pressure in the range from 50 to 1000 kg/cm$^2$ and preferably under a pressure in the range from 100 to 600 kg/cm$^2$.

The compositions according to the invention are preferably prepared in two stages: in the first stage, the active materials, additives and fillers are mixed, optionally with grinding or micronization, and in the second stage the premix thus obtained is in turn mixed with the disintegrating agent in the absence of any grinding effect. In this way, the shape of the starch grains is not altered by deformation or fragmentation which, as will be seen in the examples, considerably improves the concentration of active material in the sprayed liquid and the uniformity of the disintegration rate.

The compact compositions according to the invention may be used in the form of cartridges in appliances of, for example, the long-barrel spray gun type used by amateur gardeners, comprising a mixing device in which the stream of water comes into contact with the suitably shaped surface of the composition during the compression stroke.

Devices of this type may vary according to whether the compact composition or cartridge has a variable or constant disintegration surface.

One example of a device of the first type is the device described in German Patent Specification 1,211,603, while the device described in French Patent Specification 74.19,647 is an example of the second type of device.

The following examples illustrate the compositions according to the invention and the process for their preparation.

EXAMPLE 1

An insecticide mixture with the following composition (by weight) is prepared:

| | | |
|---|---|---|
| Malathion: 5-(1,2-di-[ethoxycarbonyl]-ethyl)-dimethyl-phosphorothiolothionate | 15 | % |
| Lindane (γ-isomer of hexachlorocyclohexane) | 4 | % |
| maize starch | 30 | % |
| talcum | 24.5 | % |
| kaolin | 4 | % |
| absorbent silica | 13 | % |
| naphthalene sulphonate (wetting agent) | 3.2 | % |
| condensate of 10 molecules of ethylene oxide with nonyl phenol(wetting agent) | 0.3 | % |
| calcium lignosulphate (deflocculant) | 3 | % |
| sodium isopropyl naphthalene sulphonate (dispersant) | 3 | % |

The malathion, being liquid, is first applied by impregnation to the silica. The mixture of active materials, starch and additives is homogenized for 30 minutes in a paddle mixer and then compressed under a pressure of 125 bars into cylindrical pellets weighing approximately 10 g. Five of these pellets are successively introduced into the magazine of a mixing device connected to a spray nozzle of the type described in French patent application No. 74.19,647, in which the pesticide cartridge has a constant disintegration surface. The device is connected to a running water supply, followed by spraying in fractions of 500 ml into a graduated vessel.

The test is repeated three times, which substantially corresponds to exhaustion of the cartridge. The contents of each vessel are evaporated and the dry extract weighed.

The following results are obtained in this way, representing an average value based on the five cartridges.

| volume of water collected in ml | Weight of solid material collected in g | Ratio of weight to volume (disintegration rate in g/l) |
|---|---|---|
| 500 | 2.7 | 5.40 |
| 1000 | 5.3 | 5.30 |
| 1500 | 8.2 | 5.45 |
| 2000 | 10.5 | 5.25 |

This table shows, on the one hand, the high level of uniformity of the quantity of solid material disintegrated per volume of water and, on the other hand, that the disintegration rate amounts to between 5 and 5.5 g/l.

EXAMPLE 2

A fungicide mixture with the following composition (by weight) is prepared:

| | | |
|---|---|---|
| dicofol (2,2,2-trichloro-1,1-di-(4-chlorophenyl)-ethanol) | 12 | % |
| rice starch | 30 | % |
| talcum | 42 | % |
| sodium naphthalene sulphonate | 2 | % |
| potassium isopropyl naphthalene sulphonate | 3 | % |
| kaolin | 3 | % |
| absorbent silica | 8 | % |

The mixture is homogenized, compressed and tested in the same way as in the preceding example. The results obtained are set out in the following table:

| Volume of water collected in ml | Weight of solid material collected in g | Ratio of weight to volume (disintegration rate in g/l) |
|---|---|---|
| 500 | 1.9 | 3.8 |
| 1000 | 3.4 | 3.4 |
| 1500 | 5.6 | 3.7 |
| 2000 | 7.8 | 3.9 |

In this case, the quantity of material disintegrated amounts to between 3.5 and 4 g/l, disintegration taking place with a high level of uniformity.

EXAMPLE 3

A fungicide mixture with the following composition (by weight) is prepared:

| | | |
|---|---|---|
| manebe (manganese ethylene-1,2-bis-dithio-carbamate) | 47 | % |
| benomyl (methyl-N-(1-n . butyl carbamoyl-2-benz-imidazole)-carbamate) | 6 | % |
| potato starch | 39 | % |
| glucose | 5 | % |
| isopropyl naphthalene sulphonate | 2 | % |
| naphthalene sulphonate | 1 | % |

The mixture is homogenized and then compressed under a pressure of 165 bars. The pellets obtained are then tested in the same way as in Example 1. The results obtained are set out in the following table:

| Volume of water collected in ml | Weight of solid material collected in g | Ratio of weight to volume (disintegration rate in g/l) |
|---|---|---|
| 500 | 2.6 | 5.2 |
| 1000 | 5.5 | 5.5 |
| 1500 | 8.3 | 5.55 |
| 2000 | 10.8 | 5.4 |

This table shows that the disintegration rate amounts to around 5.3 g/l with a high level of uniformity.

EXAMPLE 4

The influence of grinding upon the disintegration rate is illustrated by the following test:

The three separate fungicide formulations with the following common composition (by weight) are prepared:

| | | |
|---|---|---|
| manebe (manganese-ethylene-bis-dithio-carbamate), 85% commercial grade | 23.5 | % |
| triturated sulphur | 30.0 | % |
| maize starch | 21.5 | % |
| talcum | 25 | % |

These formulations, designated $F_1$, $F_2$ and $F_3$, are prepared in two stages, the first stage being common and comprising mixing the manebe, the sulphur and the talcum in a blade mixer. In a second stage, the premix is in turn mixed for 30 minutes with maize starch in a micronizer in the case of $F_1$ (95% of the particles smaller than 10 microns),
in an Alpine type mill in the case of $F_2$ (95% of the particles smaller than 50 microns),
in a simple paddle mixer in the case of $F_3$ (particle size not reduced).

Each of these compositions is then converted under a pressure of 487 bars into compact cylindrical cartridges 28 mm in diameter each weighing 20 grams.

These cartridges are then covered by thermoforming in vacuo with an 80 microns thick polyethylene film and introduced into a spray gun for amateur gardeners of the type described in French patent application 74.19,657 in such a way that the disintegration surface is constant. The spray gun is connected to a water supply under a pressure of 3 bars so as to obtain a throughput of about 0.4 to 0.5 liter/minute. The water inlet is opened by means of a trigger so that the cartridge is disintegrated and the disintegrated substance sprayed in the form of a fine mist. The average volume required to exhaust the cartridge and the standard deviation in liters for a series of tests are then determined, each figure being the average result of 8 tests.

The results are set out in the following table:

| Formulation | Mean volume in liters | Standard deviation in liters | Throughput l/minute |
| --- | --- | --- | --- |
| $F_1$ | 4.32 | 0.44 | 0.42 |
| $F_2$ | 2.87 | 0.38 | 0.44 |
| $F_3$ | 2.07 | 0.20 | 0.44 |

This table clearly shows that, at a constant throughput, formulation $F_1$ containing micronized starch requires a disintegration volume more than 1.5 times greater than that required for formulation $F_2$ and more than twice that required for formulation $F_3$. In other words, for the same composition, formulation $F_3$ enables twice the quantity of active material to be applied to the plant which is of particular advantage for gardening formulations which, since they are often of a multipurpose character, have to contain more active material.

In addition, notation of the standard deviation shows that the reducton and, a fortiori, the absence of a grinding effect during mixing of the starch with the premix of active materials considerably improves the uniformity of disintegration.

These results show that, according to the invention, it is important that the starch grains should not be fragmented by grinding. Accordingly, the apparatus used for mixing the active materials and starch must be able to carry out this operaton without altering the shape and size of the grains.

Similar results were obtained with the following compositions:

EXAMPLE 5

| Combined insecticide/fungicide composition | |
| --- | --- |
| 85 % commercial-grade manebe | 23.5 |
| triturated sulphur | 30.0 |
| commercial-grade 5-(6-chloro-2-oxobenz-oxazolin-3-yl)-methyl diethyl phosphorothiolthionate (phosalone) | 6.0 |
| talcum | 12.5 |
| maize starch | 28.0 |
| | 100.0 | mean volume: 1.99 l, standard deviation: 0.14 l

EXAMPLE 6

| Insecticide composition | |
| --- | --- |
| Commerical-grade phosalone | 6.0 |
| absorbent synthetic silica | 6.0 |
| kaolin colored by methylene blue | 3.0 |
| talcum | 35.0 |
| rice starch | 50.0 |
| | 100.0 | mean volume: 2.06 l, standard deviation: 0.15 l

EXAMPLE 7

| Fungicide composition | |
| --- | --- |
| 83% commercial-grade 2,2,2-trichloro-1,1-di-(4-chlorophenyl)-ethanol (dicofol) | 5.9 |
| absorbent synthetic silica | 4.1 |
| kaolin colored with methylene blue | 32.0 |
| maize starch | 55.0 |
| | 100.0 | mean volume: 1.92 l, standard deviation: 0.12 l

EXAMPLE 8

| Combined insecticide/fungicide composition | |
| --- | --- |
| γ-isomer of hexachlorocyclohexane (lindane), 95 % commercial-grade | 2.3 |
| 85 % commercial-grade methyl-1-naphthyl carbamate (carbaryl) | 8.9 |
| zinc ethylene-1,2-bis-dithiocarbamate (zinebe), 93 % | 21.5 |
| triturated sulphur | 30.0 |
| talcum | 10.0 |
| potato starch | 27.3 |
| | 100.0 | mean volume: 2.05 l, standard deviation: 0.09 l

EXAMPLE 9

| Fungicide composition for vine | |
| --- | --- |
| copper oxychloride containing 53 % of copper metal | 28.0 |
| 93 % commercial-grade zenebe | 5.4 |
| 85 % commercial-grade manebe | 5.9 |
| talcum | 10.0 |
| corn starch | 50.7 |
| | 100.0 | mean volume: 3.80 l, standard deviation: 0.15 l

In this case, the cartridges weigh 40 grams but are otherwise identical.

EXAMPLE 10

| Selective herbicide for the treatment of grass | |
| --- | --- |
| sodium salt of 2,4-dichlorophenoxy acetic acid (2,4-D) | 5.5 |
| sodium salt of 2-methyl-4-chlorophenoxy propionic acid | 22.0 |
| maize starch | 41.0 |
| talcum | 31.5 |
| | 100.0 |

A 40 g cartridge disintegrating into 4 liters enables 40 square meters of grass to be treated. mean disintegraton volume: 3.90 l, standard deviaton 0.2 l.

EXAMPLE 11

Selective herbicide for the treatment of grass
sodium salt of 2,4-dichlorophenoxy acetic

| Selective herbicide for the treatment of grass | |
| --- | --- |
| acid | 11.0 |
| kaolin | 3.0 |
| talcum | 35.5 |
| maize starch | 50.0 |
| | 100.0 |

A 20 g cartridge disintegrating into 2 liters enables 20 square meters of grass to be treated. average disintegration volume: 2.06 l, standard deviation: 0.1 l.

EXAMPLE 12

| Fertilizer for leaf application | |
| --- | --- |
| diammonium phosphate | 4.05 |
| urea | 2.10 |
| potassium nitrate | 3.67 |
| oligoelements (B, Cu, Fe, Mg, Mn, Mo, Zn) | 0.18 |
| starch | 20.0 |
| talcum | 70.0 |
| | 100.0 |

A 20 g cartridge disintegrates on average into 2.15 liters with a standard deviation of 0.2 l.

These examples are intended to illustrate insecticide and/or fungicide or herbicide compositions, although compositions with a growth-regulating effect on plants and, in addition, the same properties as the compositions described also form part of the invention.

The compositions of Examples 5 to 12 do not contain any wetting agent and/or dispersant and/or flocculant, because experience has shown that these additives are not indispensable and are only useful when the active material is extremely hydrophobic.

These examples illustrate the remarkable properties of the compositions according to the invention, namely their ability to disintegrate uniformly at an adequate disintegration rate.

These compositions may thus be used with a variety of phytosanitary active materials for the treatment or cultures of all kinds, more especially trees, vegetables and flowers.

This application, combining simplicity, convenience and safety both for the user and for the plant, makes the compositions particularly suitable for the treatment of amateur gardens.

We claim:

1. A solid phytosanitary composition compacted into single doses for agricultural application intended to be progressively disintegrated by contact with a stream of water and containing a few to 80% by weight of an active material selected from the group consisting of a herbicide, growth regulator, and fertilizer, a solid non-hydrophilic filler of which talcum is the major component and 20-60% by weight of a solid water-insoluble starch.

2. A composition claimed in claim 1, wherein the starch is selected from the group consisting of maize, corn, rice and potato starch.

3. A composition as claimed in claim 2, wherein the starch is not ground.

4. A process for the preparation of a phytosanitary composition of the type claimed in claim 1, comprising in a first stage mixing the active material and the filler with grinding or micronization to form a premix, and, in a second stage, mixing the premix with the starch without deformation or fragmentation of the starch grains by grinding, and compressing the mixture into single doses under a pressure of from 50 to 100 bars.

5. A solid phytosanitary composition compacted into single doses for agricultural, application intended to be progressively disintegrated by contact with a stream of water and containing a few to 80% by weight of an active material selected from the group consisting of an insecticide, fungicide and bactericide, a solid non-hydrophilic filler of which talcum is the major component and 20-60% by weight of a solid, water insoluble starch.

6. A composition as claimed in claim 1 which includes a wetting agent, dispersant or deflocculant.

* * * * *